United States Patent
Yoshikawa

(10) Patent No.: US 11,490,876 B2
(45) Date of Patent: Nov. 8, 2022

(54) ULTRASONIC DIAGNOSTIC DEVICE AND METHOD FOR EVALUATING PHYSICAL PROPERTIES OF BIOLOGICAL TISSUE

(71) Applicant: Hitachi, Ltd., Tokyo (JP)

(72) Inventor: Hideki Yoshikawa, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 175 days.

(21) Appl. No.: 16/642,395

(22) PCT Filed: Oct. 12, 2018

(86) PCT No.: PCT/JP2018/038161
§ 371 (c)(1),
(2) Date: Feb. 27, 2020

(87) PCT Pub. No.: WO2019/087741
PCT Pub. Date: May 9, 2019

(65) Prior Publication Data
US 2020/0187909 A1    Jun. 18, 2020

(30) Foreign Application Priority Data

Nov. 2, 2017   (JP) .............................. JP2017-212637

(51) Int. Cl.
*A61B 8/08*   (2006.01)
*A61B 8/14*   (2006.01)
(52) U.S. Cl.
CPC ............ *A61B 8/485* (2013.01); *A61B 8/0858* (2013.01); *A61B 8/14* (2013.01); *A61B 8/5207* (2013.01)
(58) Field of Classification Search
CPC ......... A61B 8/485; A61B 8/0858; A61B 8/14; A61B 8/5207
See application file for complete search history.

(56) References Cited

U.S. PATENT DOCUMENTS

2009/0143675 A1* 6/2009 Suzuki .................. A61B 8/485
                                                            600/437
2009/0163805 A1* 6/2009 Sunagawa ........... G01S 15/8979
                                                            600/438

(Continued)

FOREIGN PATENT DOCUMENTS

CN          106999162 A      8/2017
JP          2015524740 A     8/2015

(Continued)

OTHER PUBLICATIONS

International Preliminary Report on Patentability received in corresponding International Application Mo PCTIJP2018/038161 dated May 5, 2020.

(Continued)

*Primary Examiner* — Katherine L Fernandez
*Assistant Examiner* — Brooke Lyn Klein
(74) *Attorney, Agent, or Firm* — Mattingly & Malur, PC

(57) ABSTRACT

Provided is a technique for evaluating properties of a membranous tissue or a surface of the tissue in a biological body by ultrasonic waves. A method of the invention includes setting one or more measurement points on a surface of the biological tissue to be inspected; measuring, in a state in which an elastic wave propagates to the biological tissue, at least a surface wave of the elastic wave by measuring a displacement of the biological tissue at the measurement point by using an ultrasonic wave; and calculating an index value indicating physical properties of the biological tissue by using the measured displacement.

5 Claims, 12 Drawing Sheets

(56) References Cited

U.S. PATENT DOCUMENTS

| | | | | |
|---|---|---|---|---|
| 2011/0263978 | A1* | 10/2011 | Chen | A61B 8/485 |
| | | | | 600/438 |
| 2012/0232387 | A1* | 9/2012 | Miyachi | A61B 5/02007 |
| | | | | 600/438 |
| 2013/0317361 | A1* | 11/2013 | Tabaru | G01S 7/52042 |
| | | | | 600/438 |
| 2014/0094702 | A1* | 4/2014 | Kim | A61B 8/08 |
| | | | | 600/438 |
| 2015/0133782 | A1* | 5/2015 | Yoshikawa | A61B 8/5223 |
| | | | | 600/438 |
| 2015/0148675 | A1 | 5/2015 | Haupt | |
| 2016/0262706 | A1 | 9/2016 | Zhao et al. | |
| 2017/0224304 | A1* | 8/2017 | Sonoyama | A61B 8/485 |
| 2017/0333004 | A1* | 11/2017 | Yoshikawa | A61B 5/318 |
| 2019/0046160 | A1* | 2/2019 | Li | A61B 8/485 |
| 2019/0254629 | A1* | 8/2019 | Li | A61B 8/5207 |

FOREIGN PATENT DOCUMENTS

| | | |
|---|---|---|
| JP | WO2013153968 A1 | 12/2015 |
| WO | 2013/153968 A1 | 10/2013 |

OTHER PUBLICATIONS

H. Zhao, et al., "External Vibration Multi-Directional Ultrasound Shearwave Elastography (EVMUSE): Application in Liver Fibrosis Staging", IEEE Transaction on Medical imaging, vol. 33, No. 11, Nov. 2014, pp. 2140-2148.

H. Kanai, "Propagation of Spontaneously Actuated Pulsive Vibration in Human Heart Wall and In Vivo Viscoelasticity Estimation", IEEE Transactions on Ultrasonic Ferroelectrics, and Frequency Control, vol. 52, No. 11, Nov. 2005, pp. 1931-1942.

I. Nenadic, et al., "Lamb Wave Shearwave Dispersion Ultrasound Vibrometry (SDUV) Validation Study", 32nd Annual International Conference of the IEEE EMBS, Buenos Aires, Argentina, Aug. 31, 2010-Sep. 4, 2010, pp. 45-48.

Jun-keen Jang, et al., Comparison of techniques for estimating shear-wave velocity in arterial wall using shear-wave elastography—FEM and phantom study, IEEE International Ultrasonics Symposium Proceedings, 2015, vol. 1, pp. 339-342.

X. Zhange, et al., Quantitative surface wave method for measuring local viscoelasticity of lungs, IEEE International Ultrasonics Symposium Proceedings, vol. 1, 2009, pp. 479-482.

Hiroshi Kanai, et al., Viscoelasticity Measurement of Heart Wall in in vivo, Proc IEEE Ultrasonic Symposium, vol. 1, 2004, pp. 482-485.

International Search Report of PCT/JP2018/038161 dated Dec. 11, 2018.

Chinese Office Action received in corresponding Chinese Application No. 201880055967.6 dated Jan. 26, 2022.

* cited by examiner

[FIG. 1]
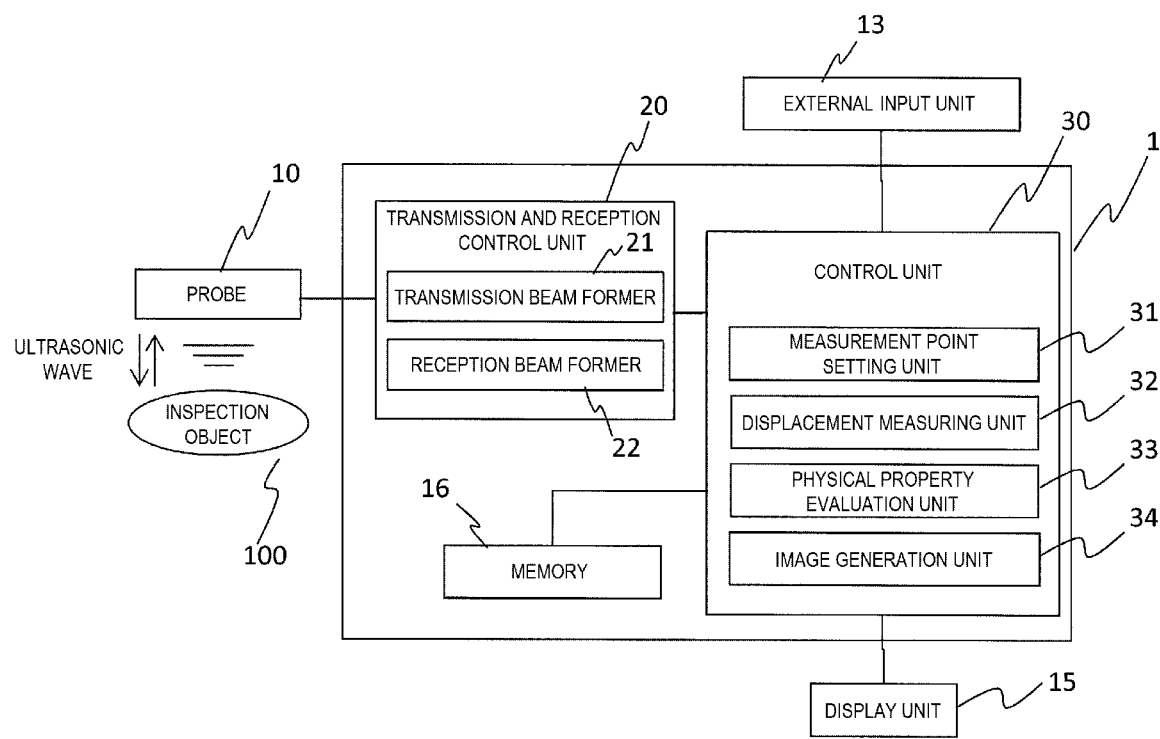

[FIG. 2]
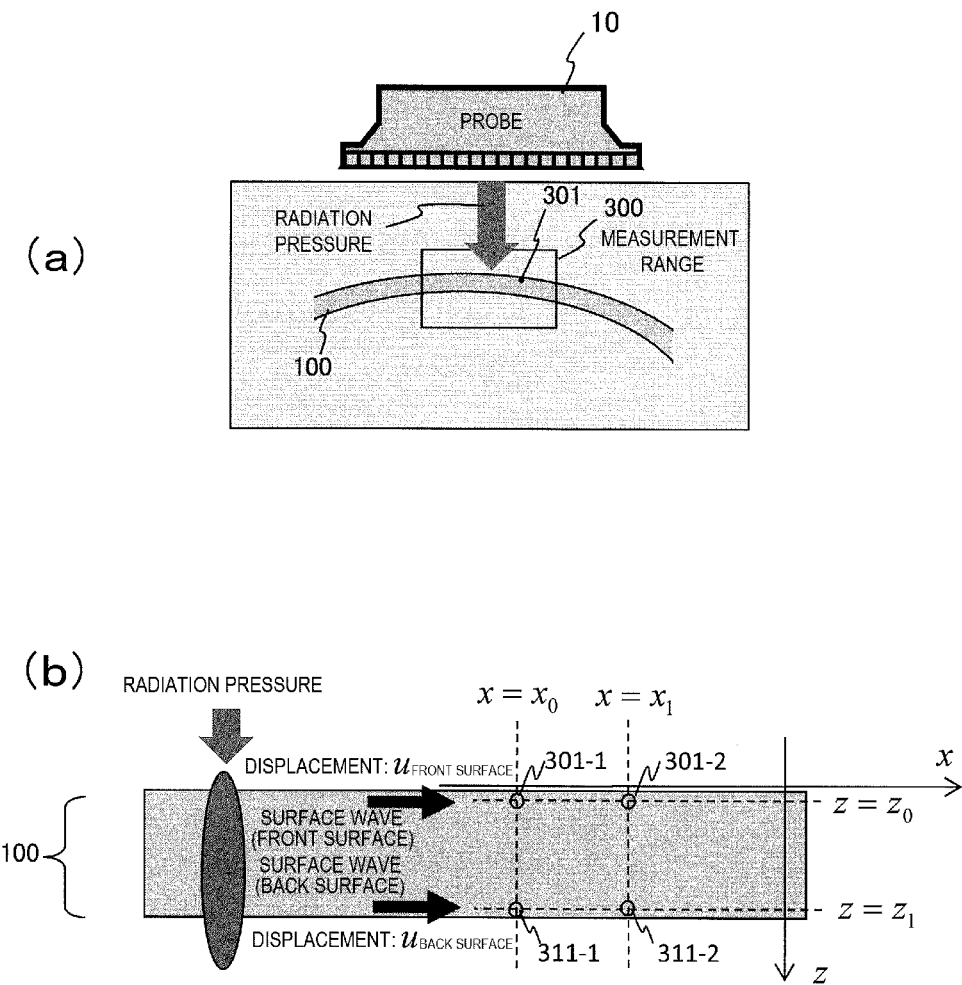

[FIG. 3]

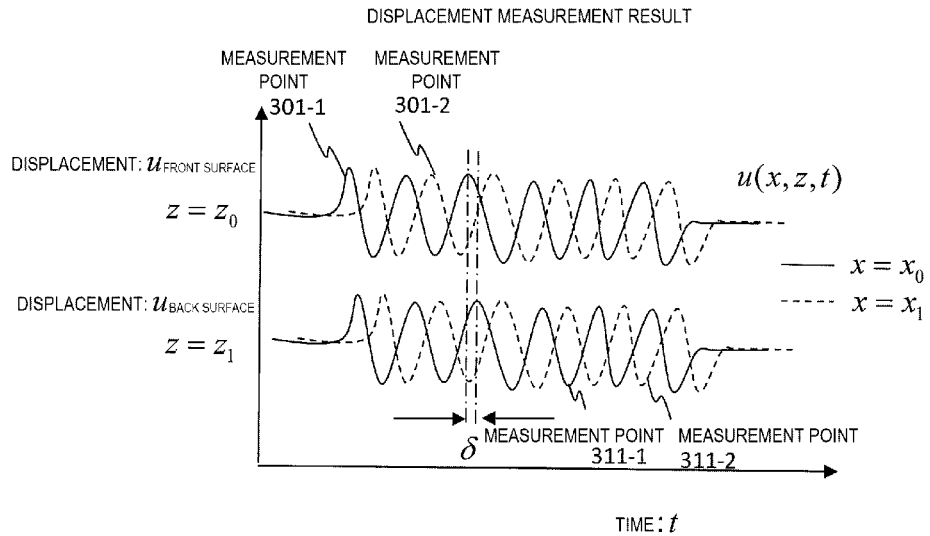

DISPLACEMENT MEASUREMENT RESULT

INDEX VALUE INDICATING PHYSICAL PROPERTIES OF MEMBRANE

FRONT SURFACE VELOCITY (VISCOELASTICITY)  $V_{z0} = \dfrac{\Delta[u(x_0,z_0,t),u(x_1,z_0,t)]}{x_0 - x_1}$ BACK SURFACE VELOCITY (VISCOELASTICITY)  $V_{z1} = \dfrac{\Delta[u(x_0,z_1,t),u(x_1,z_1,t)]}{x_0 - x_1}$ PHASE DIFFERENCE BETWEEN
FRONT SURFACE AND BACK SURFACE  $\delta = \Delta[u(x_0,z_0,t),u(x_0,z_1,t)]$ $\Delta[a,b]$: TIME DIFFERENCE OF A AND B, CROSS-CORRELATION CALCULATION)

[FIG. 4]
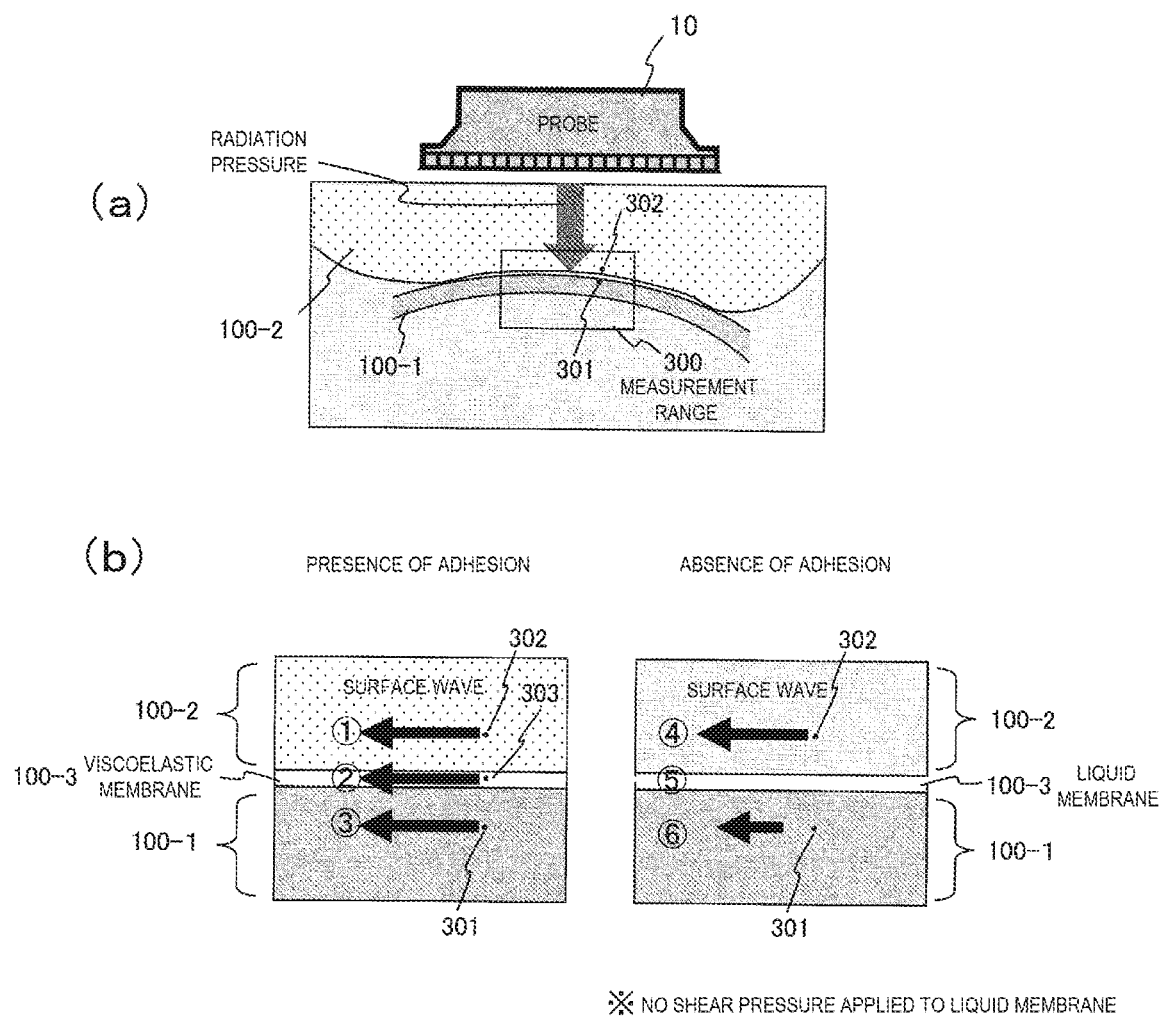

[FIG. 5]
(a)
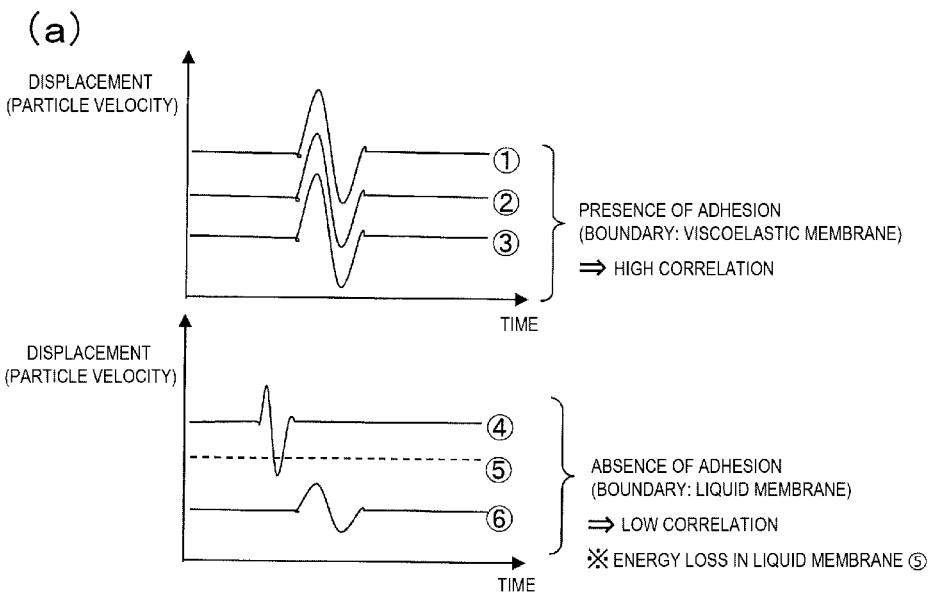
(b)
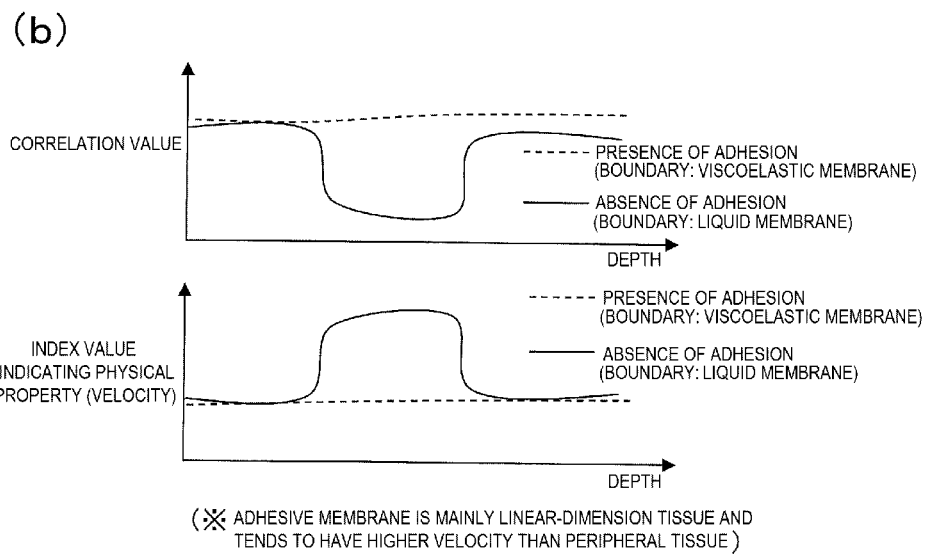
(※ ADHESIVE MEMBRANE IS MAINLY LINEAR-DIMENSION TISSUE AND TENDS TO HAVE HIGHER VELOCITY THAN PERIPHERAL TISSUE)

[FIG. 6]
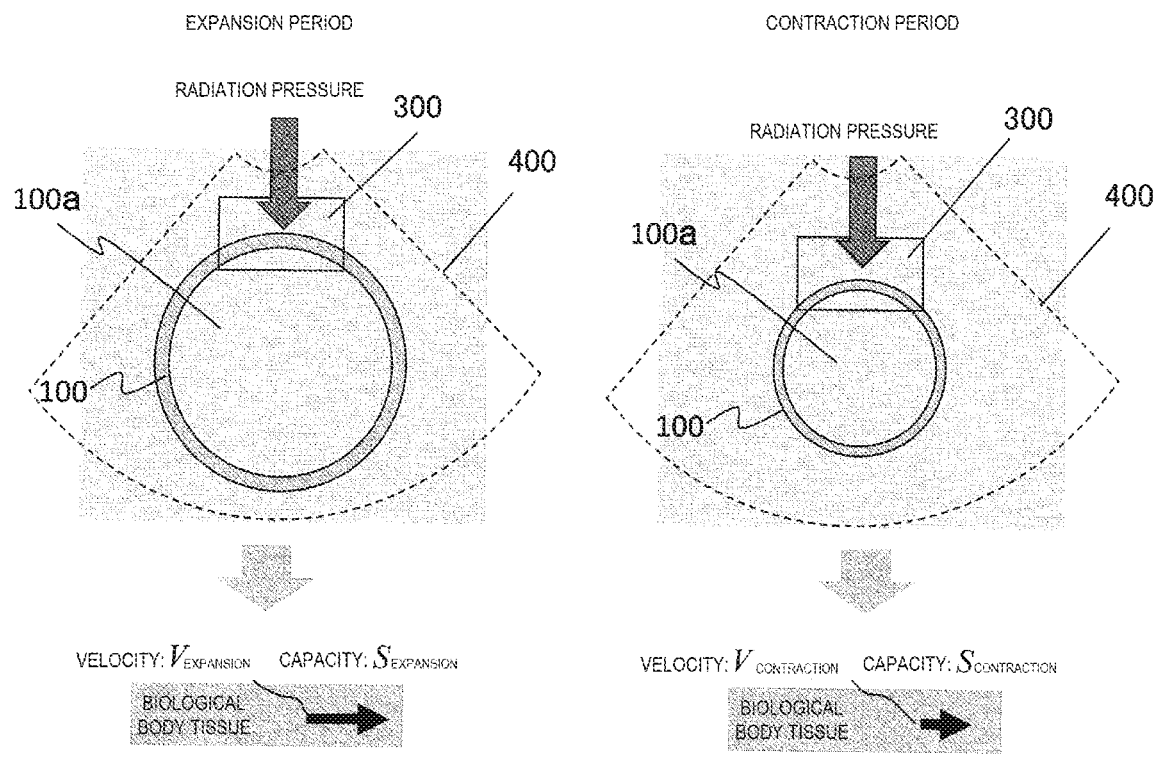

[FIG. 7]
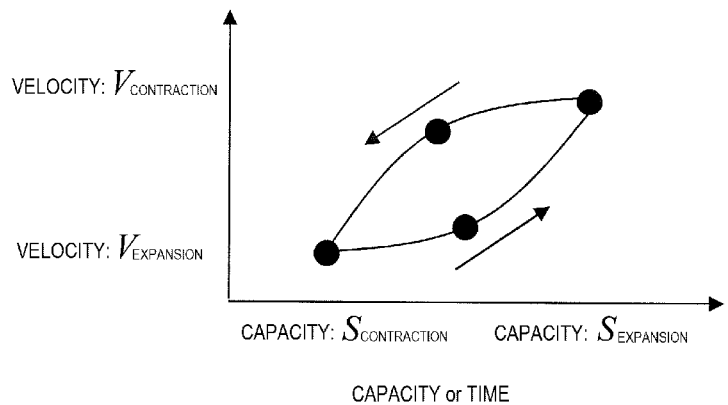
CONTRACTION ACCELERATION: $\dfrac{\partial V_{CONTRACTION}}{\partial t}$
EXPANSION ACCELERATION: $\dfrac{\partial V_{EXPANSION}}{\partial t}$
HYSTERESIS CHARACTERISTIC: $\int_{t_{CONTRACTION}}^{t_{EXPANSION}} \overline{V_{CONTRACTION}}\, dV - \int_{t_{CONTRACTION}}^{t_{EXPANSION}} \overline{V_{EXPANSION}}\, dV$

[FIG. 8]
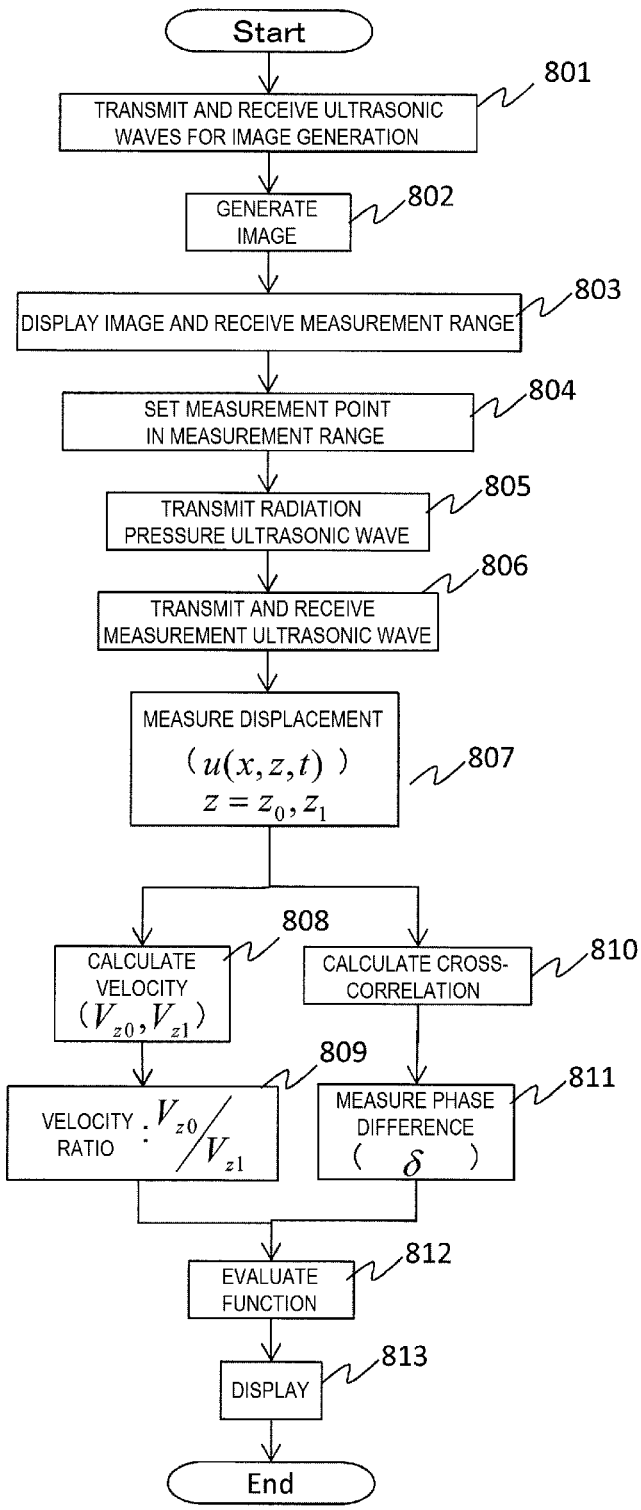

[FIG 9]
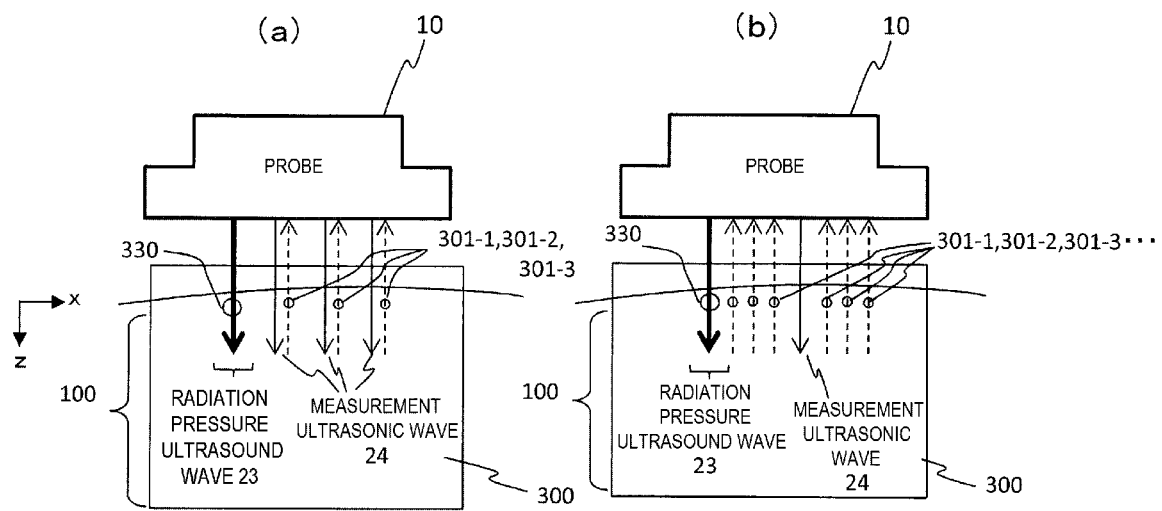

[FIG. 10]
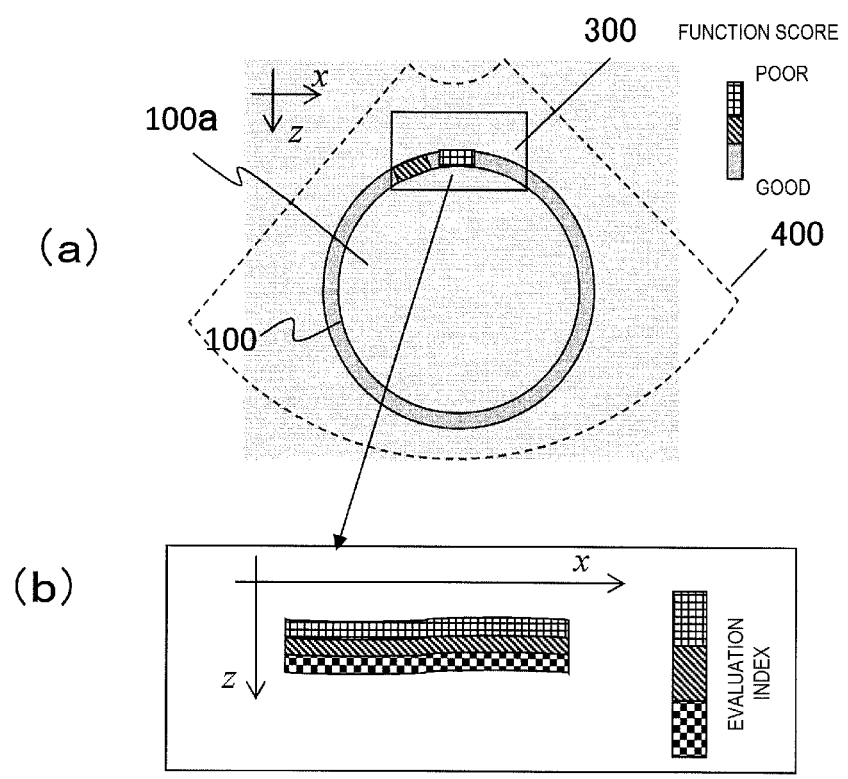

[FIG. 11]
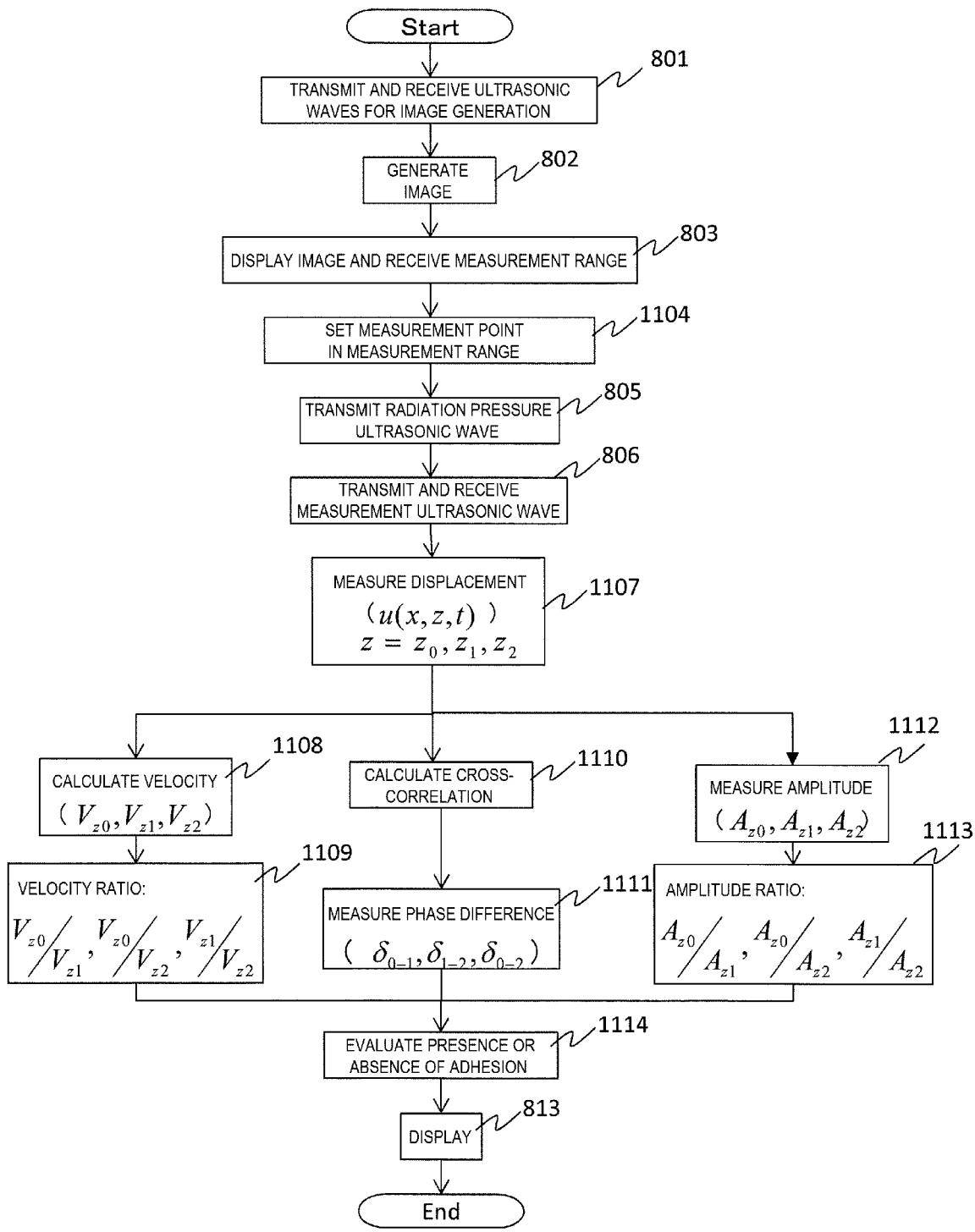

[FIG. 12]
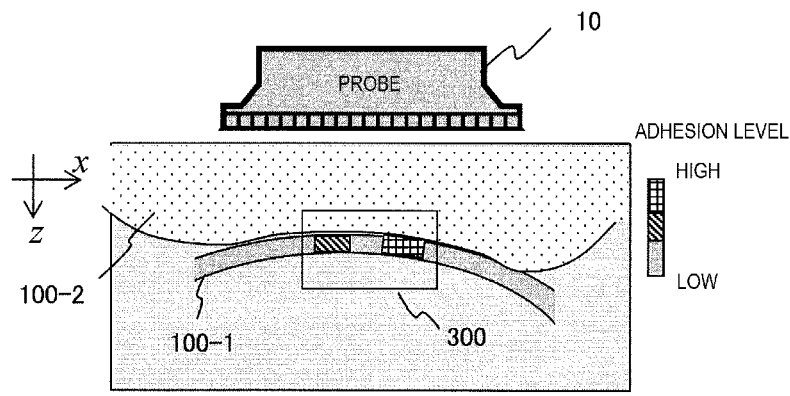
[FIG. 13]
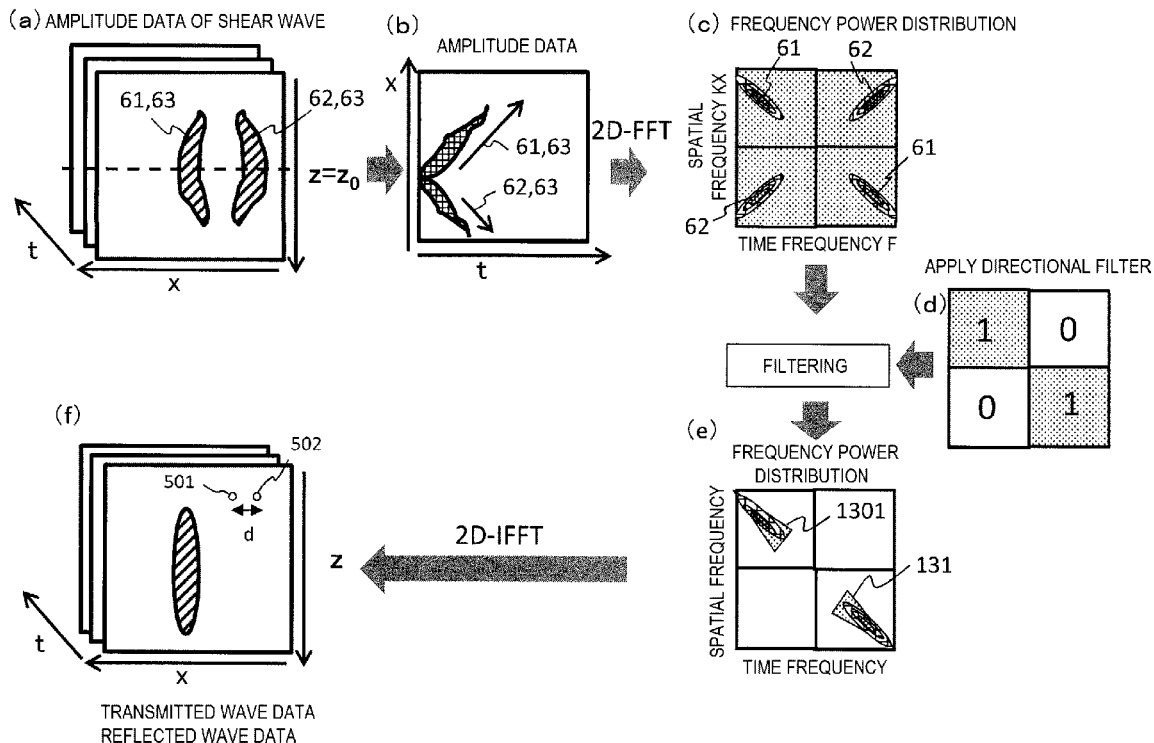

ULTRASONIC DIAGNOSTIC DEVICE AND METHOD FOR EVALUATING PHYSICAL PROPERTIES OF BIOLOGICAL TISSUE

TECHNICAL FIELD

The present invention relates to an ultrasonic diagnostic device and a technique for evaluating properties of a biological tissue by generating an elastic wave in a subject and measuring a tissue displacement in accompany with propagation.

BACKGROUND ART

Medical image display devices typified by an ultrasonic imaging device, an Magnetic Resonance Imaging (MRI) device, and an X-ray CT (Computed Tomography) device are widely used as devices for presenting information in an invisible biological body in a form of numbers or images. Among these devices, the ultrasonic imaging device has a high temporal resolution as compared with the other devices and has a performance of being capable of imaging a pulsating heart without blurring.

Ultrasonic waves propagating in a biological body are mainly divided into longitudinal waves and transverse waves. An ultrasonic imaging device in the related art mainly uses information of longitudinal waves (sound speed of about 1540 m/s) to visualize a tissue morphology and measure a blood flow velocity.

In recent years, there is a growing attention for a technique of evaluating an elastic modulus of a tissue using the transverse waves (hereinafter referred to as shear waves), and a clinical use for chronic liver diseases and cancers is in progress. In the technique, a shear wave is generated inside a tissue to be measured, a displacement of the tissue is measured, a propagation velocity is calculated from the displacement, and an elastic modulus of the tissue is calculated from the propagation velocity to evaluate the tissue. Methods for generating the shear wave are roughly classified into a mechanical method and a radiation pressure method. The mechanical method is a method that generates a shear wave by applying a vibration of about 1 kHz to a body surface by using a vibrator or the like, which requires a driving device as a vibration source. On the other hand, in the radiation pressure method, an acoustic radiation pressure is applied to the biological body by using focused ultrasonic waves that allow ultrasonic waves to be locally concentrated in the tissue, and the shear wave is allowed to be generated using a tissue displacement that occurs instantaneously.

Non-Patent Document 1 discloses a method of extracting a specific component from a wavefront of a shear wave propagating through an object to be inspected. Specifically, in the method, a spatial distribution of a wavefront amplitude of the propagating shear wave is converted into a frequency space having spatial frequencies in an azimuth direction and a depth direction as a vertical axis and a horizontal axis and the spatial frequency space is divided at equal angles. Then, the wavefront amplitude in a real space is extracted in the propagation direction of the shear wave by retransforming each component (wavefront amplitude) included in the divided spaces into the real space.

As in Non-Patent Document 1, Patent Document 1 discloses a technique of exciting a shear wave for a purpose of measuring mechanical characteristics of an inspection object, measuring a displacement from x to z in a real space, converting a space from a spatial frequency k to a time frequency f, and extracting a shear wave propagating in a specific direction at a predetermined speed by applying a directional filter.

Non-Patent Document 2 discloses a technique for evaluating myocardial properties. A heart repeats periodic beating by transmitting an electric signal from a sinoatrial node through myocardial tissue such as septal tissue separating left and right of the heart. Although an elastic wave is transmitted to the septal tissue with the transmission of the electric signal, the technique of Non-Patent Document 2 measures the displacement of the septal tissue during the propagation of the elastic wave to evaluate a function of the heart.

Non-Patent Document 3 also discloses an elastic wave measurement technique for a purpose of tissue properties of a heart. In the technique, a surface wave is generated using a vibrator inserted into a biological tissue simulated tissue, and the displacement of the medium is measured. A displacement measurement result is frequency-analyzed, and a frequency dispersion of a velocity of the surface wave is calculated.

PRIOR ART LITERATURE

Patent Literature

PTL 1: JP-T-2015-524740

Non-Patent Literature

NPTL 1: H. Zhao, et al., IEEE Trans. Med. Imaging, 33, 11, (2014)
NPTL 2: H. Kanai, IEEE Trans. Ultrason. Ferr. Freq. Contll, vol. 52, no. 11, (2005) pp. 1931
NPTL 3: I. Nenadic, et. al., 32nd Annual International Conference of the IEEE EMBS (2010) pp. 45

SUMMARY OF INVENTION

Technical Problem

Among tissues in a biological body, a bladder or a heart has a pump function related to urination and blood circulation, and a wall structure thereof is formed of muscular layer tissue. When the properties of the muscle layer tissue are abnormal, the pump function is reduced and symptoms such as dysuria and arrhythmia appear.

A urological disorder is a disease that increases in importance, especially during an advancement of elderly society. For example, since a tachycardia or a residual urine feeling is not a life-threatening symptom, a patient may not consult a doctor and the symptom may be not diagnosed as a disease. In such a case, an appropriate treatment such as medication is not performed on the patient. However, since abnormality of a urination relationship is an important factor that significantly lowers quality of life (QOL), a simple diagnosis method is required as much as possible.

Further, in the case of a heart disease, it is necessary to perform a risk determination at an early stage as much as possible because it is life-threatening. For a heart, a blood flow or a pump function as a heart (cardiac wall motion under pulsation) is often examined, and risk determination may be performed at an early stage by accurately evaluating properties of myocardium.

There is also a peritoneum between body surface tissue (fat and muscle) and a body organ (for example, a liver), and some patients may have adhesions between the peritoneum and the body organ or between body organs. Although laparoscopic surgery has been widely used as a minimally invasive treatment method which causes a small physical burden during advancement of an aging society, information on the presence or absence of adhesions in the body and an adhesion position is important preoperative information to ensure a device route for inserting a forceps, a scalpel and a camera or the like to an affected area.

What is common to the bladder, the heart, and the adhesion membrane is that a focused tissue is in a form of a membrane (or a planar plate having a certain thickness). In a case of focusing on a central portion of biological tissue that is sufficiently larger than the wavelength size of the elastic wave, an evaluation method suitable for a shear wave as in the related art may be used since a real wave (a compressional wave or shear wave) is a main component as a type of an elastic wave propagating to a region of interest. However, in order to evaluate the membranous tissue using ultrasonic waves, it is necessary to detect the influence of not only the real wave but also a surface wave (rayleigh wave or rub wave) and use an evaluation method suitable for the wave, since the thickness of the evaluation object is smaller than the wavelength size of the elastic wave.

In the technique described in Patent Document 1 and Non-Patent Document 1, the shear wave is assumed as an elastic wave to be measured since an object is a relatively large tissue such as a liver. However, it is not disclosed in Patent Document 1 or Non-Patent Document 1 to actively measure waves other than shear waves and perform analysis in consideration of properties of the membranous tissue in order to evaluate the membranous tissue.

The technique of Non-Patent Document 2 focuses on a septal tissue of a heart, which is similar to the present invention in terms of the membranous tissue, and evaluates the septal tissue in the same manner as in a case of a large tissue.

The technique of Non-Patent Document 3 focuses on surface waves and processing contents thereof are the same as those for shear waves described in Patent Document 1 and Non-Patent Document 1. No processing taking properties of surface waves into consideration is performed.

An object of the present invention is to provide a technique for evaluating properties of a membranous tissue or a surface of a tissue in a biological body by ultrasonic waves.

Solution to Problem

According to the invention, an ultrasonic diagnostic device includes a measurement point setting unit that is configured to set one or more measurement points on a surface of a biological tissue to be inspected; a displacement measuring unit that is configured to measure, in a state in which an elastic wave is propagated to the biological tissue, at least a surface wave of the elastic wave by measuring a displacement of the biological tissue at the measurement point by using an ultrasonic wave; and a physical property evaluation unit that is configured to calculate an index value indicating physical properties of the biological tissue by using the measured displacement.

Advantageous Effect

According to the invention, properties of a membranous tissue or a surface of a tissue in a biological body can be evaluated by ultrasonic waves.

BRIEF DESCRIPTION OF DRAWINGS

FIG. 1 is a block diagram of a configuration example of an ultrasound imaging diagnosis device according to an embodiment.

FIG. 2(a) is an explanatory view showing irradiation of radiation pressure ultrasonic waves to a membranous biological tissue, and FIG. 2(b) is an explanatory view showing propagation of a surface wave generated by the radiation pressure ultrasonic waves.

FIG. 3 is a graph showing a time change of a displacement measured at a measurement point of a biological tissue 100.

FIG. 4(a) is an explanatory view showing irradiation of radiation pressure ultrasonic waves at a boundary between two biological tissues, and 4(b) is an explanatory view showing cases where a surface wave generated by radiation pressure ultrasonic waves propagates on a surface of two biological tissues having adhesion and having no adhesion.

FIG. 5(a) is a graph showing a displaced waveform caused by propagation of a surface wave through a boundary between two biological tissues in a case where there is adhesion and in a case where there is no adhesion, and 5(b) is a graph showing a correlation value of a displacement waveform near the boundary between two biological tissues and a variation of an index value indicating physical properties in a case where there is adhesion and in a case where there is no adhesion.

FIG. 6 shows a change in a shape of the biological tissue 100 as a bladder in an expansion period and in a contraction period, and a change in an index value indicating physical properties (velocity).

FIG. 7 shows a change (hysteresis) in an index value indicating physical properties (velocity) and capacity in expansion and contraction periods of the bladder.

FIG. 8 is a flowchart showing operation of an ultrasound diagnostic device according to a first embodiment.

FIGS. 9(a) and 9(b) are illustrative views showing methods of transmitting and receiving ultrasonic waves for measurement in the first embodiment.

FIGS. 10(a) and 10(b) are an example of a display method showing a function of the biological tissue obtained according to the first embodiment.

FIG. 11 is a flowchart showing operation of an ultrasonic diagnostic device according to a second embodiment.

FIG. 12 shows an example of a display method showing presence or absence of adhesion of biological tissues obtained according to the second embodiment.

FIGS. 13(a) to 13(f) are explanatory diagrams showing a procedure when a surface wave of a transmitted wave is extracted from a measurement waveform according to an embodiment.

DESCRIPTION OF EMBODIMENTS

Embodiments of the present invention will be described below with reference to the drawings.

In the present embodiment, an index value indicating physical properties is calculated and a membranous tissue or a surface of the tissue is evaluated by mainly measuring a surface wave of elastic waves propagating in a biological tissue.

FIG. 1 shows a block diagram of a configuration example of an ultrasonic diagnostic device (an ultrasonic wave transmission and reception device) according to an embodiment. As shown in FIG. 1, the ultrasonic diagnostic device according to the present embodiment includes a measurement point setting unit 31, a displacement measuring unit 32, and a physical property evaluation unit 33.

As shown in FIGS. 2(*a*) and 2(*b*), the measurement point setting unit 31 sets one or more measurement points 301 on a surface of the biological tissue 100 to be inspected. The displacement measuring unit 32 measures a displacement of the biological tissue at the measurement points 301 using ultrasonic waves in a state where an elastic wave is propagating in the biological tissue 100.

The biological tissue 100 is an elastic body, which receives vibration by some method or generates vibration due to spontaneous movement of the biological tissue 100. An elastic wave propagates in the biological tissue 100. The elastic wave has a plurality of types, in which shear waves propagate inside the biological tissue 100 and surface waves propagate on the surface of the biological tissue 100. The surface wave proceeds with characteristic vibration and an amplitude thereof, which is smaller than that of the shear wave, becomes larger as the thickness of the biological tissue becomes smaller. In addition, in modes of the surface wave, there is a mode in which a phase relationship is different between both surfaces of a membrane.

In the present embodiment, since the measurement point setting unit 31 sets the measurement point 301 on the surface of the biological tissue 100, the displacement measuring unit 32 measures a displacement of the measurement points 301 and thereby the displacement caused by the surface wave can be measured. The physical property evaluation unit 33 calculates an index value indicating physical properties of the biological tissue 100 using the measured displacement.

A velocity of an elastic wave (mainly a surface wave) propagating through the biological tissue 100, a difference in velocity of an elastic wave propagating through two or more measurement points, a phase difference of an elastic wave propagating through two or more measurement points, an elastic modulus of the biological tissue 100, and the like can be used as the index value indicating physical properties.

In this manner, the ultrasonic diagnostic device according to the present embodiment can accurately evaluate physical properties by measuring the surface wave when the biological tissue 100 is a membranous tissue or when the surface of the biological tissue 100 is an evaluation object.

The physical property evaluation unit 33 can determine tissue properties of the biological tissue 100 or whether an organ (for example, a heart or a bladder) constituted by the biological tissue 100 functions well by using the calculated index value indicating the physical properties.

When the biological tissue 100 is in a form of a membrane or a wall, a difference in velocity or phase of an elastic wave (mainly surface wave) propagating through measurement points on both surfaces of the biological tissue 100 in the form of a membrane or a wall can be used as the index value indicating physical properties. In this case, the measurement point setting unit 31 sets at least one measurement point 301 and at least one measurement point 311 respectively on both sides of the biological tissue 100 in a form of a membrane or a wall as shown in FIG. 2(*b*). The displacement measuring unit 32 measures the displacement at each of the measurement points 301 and 311, as shown in FIG. 3. The physical property evaluation unit 33 calculates the difference in velocity or phase of the elastic wave propagating through the measurement points 301 and 311 on both surfaces as the index value indicating physical properties by using the displacement at the measurement points 301 and 311 on both surfaces.

In addition, in the present embodiment, tissue properties of the biological tissue include presence or absence of a bonding state (for example, adhesion) between the biological tissue and the surrounding tissue, and it is possible to determine whether the biological tissue is bonded to the surrounding tissue. In this case, as shown in FIG. 4(*a*), the measurement point setting unit 31 sets measurement points 301 and 302 on respective surfaces of two biological tissues 100-1 and 100-2 at a position where the two adjacent biological tissues 100-1 and 100-2 face each other. The displacement measuring unit 32 measures a waveform of an elastic wave (mainly a surface wave) by measuring the displacement in each of the measurement points 301 and 302 (see FIGS. 4(*b*) and 5(*a*)).

As shown in a left side view of FIG. 4(*b*), when a boundary layer 100-3 between the biological tissues 100-1 and 100-2 is a viscoelastic membrane, the biological tissues 100-1 and 100-2 are bonded (for example, adhered) and displacements of both tissues are linked. Therefore, a correlation degree between displacement waveforms of the measurement points 301 and 302 and index values indicating physical properties of the measurement points 301 and 302 (for example, the velocity and the elastic modulus of the elastic wave) increase as shown in FIGS. 5(*a*) and 5(*b*).

On the other hand, as shown in a right side view of FIG. 4(*b*), when the boundary layer 100-3 between the biological tissues 100-1 and 100-2 is a liquid layer, the biological tissues 100-1 and 100-2 are not bonded and the displacements of both tissues are not linked. Therefore, the correlation degree between the displacement waveforms of the measurement points 301 and 302 and the index values indicating physical properties of the measurement points 301 and 302 (for example, the velocity and the elastic modulus of the elastic wave) decrease as shown in FIGS. 5(*a*) and 5(*b*) than in the case of adhesion.

Therefore, the physical property evaluation unit 33 determines the correlation degree between the displacement waveforms of the two measurement points 301 and 302 or the correlation degree of the index values indicating physical properties of the two measurement points 301 and 302, thereby determining presence or absence of the bonding state (for example, adhesion) of the two biological tissues by a magnitude of the correlation degree.

As shown in FIG. 4(*b*), a measurement point 303 may also be set in the boundary layer 100-3.

The measurement point setting unit 31 may set the measurement point 301 and the like on the surface of the biological tissue based on an image of the biological tissue 100. For example, the measurement point setting unit 31 can detect the surface of the biological tissue 100 or the boundary between the biological tissues 100-1 and 100-2 and set the measurement point 301 and the like by processing the image of the biological tissue 100.

As shown in FIG. 6, in a case where the biological tissue 100 constitutes an organ which has a space 100*a* therein and is capable of storing liquid or gas in and discharging liquid or gas from the space 100*a*, the physical property evaluation unit 33 determines tissue properties of the biological tissue 100 or whether the organ constituted by the biological tissue 100 functions well based on an index value indicating physical properties and a capacity of the space 100*a*. In this case, the physical property evaluation unit 33 may obtain the capacity of the space 100*a* by obtaining the magnitude of the space in the image based on the image of the biological tissue 100.

The physical property evaluation unit 33 may calculate the capacity of the space 100*a* at a plurality of time points during a period in which the biological tissue 100 stores liquid or gas in or discharges liquid or gas from the space 100a, calculate the index value indicating physical properties of the biological tissue 100 at the plurality of times, and determine whether the organ constituted by the biological tissue 100 functions well based on the capacity of the space 100a and a change in the index value. For example, as shown in FIG. 7, the physical property evaluation unit 33 performs the determination based on a shape or area of a hysteresis obtained by plotting the capacity and the change in the index value indicating physical properties of the space 100a in a space having the capacity and the index value as two axes.

Hereinafter, the configuration of the ultrasonic diagnostic device 1 according to the present embodiment will be described in more details. In the following description, a case where the biological tissue 100 is irradiated with focused ultrasonic waves to generate shear waves by acoustic radiation pressure will be described as an example.

As shown in FIG. 1, the ultrasound diagnostic device 1 according to the present embodiment includes a transmission and reception control unit 20 and a control unit 30. The ultrasound diagnostic device 1 is connected to a probe 10, an external input unit 13, and a display unit 15. The transmission and reception control unit 20 includes a transmission unit (hereinafter, referred to as a transmission beam former) 21 that generates a transmission signal to be delivered to each transducer included in the probe 10, and a reception unit (hereinafter, referred to as a reception beam former) 22 that generates a reception signal for a predetermined point in the biological tissue 100.

The control unit 30 includes the measurement point setting unit 31, the displacement measuring unit 32, the physical property evaluation unit 33, and an image generation unit 34. A memory 16 is connected to the control unit 30.

In the control unit 30, functions of the measurement point setting unit 31, the displacement measuring unit 32, the physical property evaluation unit 33, and the image generation unit 34 may be implemented by software, or a part or all of the functions may be implemented by hardware. When implemented by software, the control unit 30 includes a computer system including a processor such as a Central Processing Unit (CPU) and a Graphics Processing Unit (GPU) and the CPU or the like reads and executes a program stored in advance in the memory 16 to implement functions of the measurement point setting unit 31, the displacement measuring unit 32, the physical property evaluation unit 33, and the image generation unit 34. When implemented by hardware, the control unit 30 includes a custom IC such as an Application Specific Integrated Circuit (ASIC) or a programmable IC such as an Field-Programmable Gate Array (FPGA) and a circuit may be designed to implement at least operations of the measurement point setting unit 31, the displacement measuring unit 32, the physical property evaluation unit 33, and the image generation unit 34.

First Embodiment

An operation example of each unit of the ultrasound diagnostic device according to the first embodiment will be described with reference to FIG. 8. The first embodiment describes an example in which an index value indicating physical properties of the membranous biological tissue 100 is calculated and whether an organ constituted by the biological tissue 100 functions well is determined. The first embodiment describes the case where the control unit 30 is implemented by software as an example. FIG. 8 is a flowchart showing an overall operation of the ultrasonic diagnostic device. Further, FIGS. 9(a) and 9(b) show an example of ultrasonic waves transmitted and received by the probe 10.

As shown in FIG. 6, the control unit 30 instructs the transmission and reception control unit 20 to transmit and receive ultrasonic waves for image generation in order to generate an image of the biological tissue 100 in an image acquisition range 400 (Step 801). The transmission beam former 21 of the transmission and reception control unit 20 sets one or more transmission scanning routes in the image acquisition range 400, generates a transmission signal for emitting an ultrasonic beam along the transmission scanning route, and outputs the generated transmission signal to each transducer of the probe 10. As a result, the ultrasound beam for image generation is emitted from the probe 10 along the transmission scanning route to the image acquisition range 400 of the biological tissue 100. In the biological tissue 100, echoes of emitted ultrasonic beams are generated and received by the transducers of the probe 10. The reception beam former 21 generates focus data for a plurality of reception focal points on a plurality of reception scanning routes set in the image acquisition range 400 by performing phasing addition of a reception signal of each transducer. The image generation unit 34 generates an image of the image acquisition range 400 by setting the focus data as pixel values of pixels corresponding to positions of the reception focal points, and displays the image on the display unit 15 (Step 802).

The control unit 30 receives a position of a measurement range 300 of the biological tissue 100 from a user via the external input unit 13 as shown in FIG. 2 (Step 803). In FIG. 2, the biological tissue 100 is in a form of a membrane.

The measurement point setting unit 31 extracts an external shape of the membranous biological tissue 100 and sets the measurement point 301 and the like in the vicinity of the surface by performing image processing such as binarization processing in the measurement range 300 of the image generated by the image generation unit 34 (Step 804). Here, two or more measurement points 301-1, 301-2, 311-1, and 311-2 are set respectively on both surfaces (front surface and back surface) of the membranous biological tissue 100 in order to calculate a surface wave velocity on both surfaces of the membranous biological tissue 100 as an evaluation value indicating physical properties. In addition to the velocity, a phase difference between surface waves propagating on both surfaces is also obtained as an evaluation value indicating physical properties.

Next, as shown in FIGS. 9(a) and 9(b), the displacement measuring unit 32 sets a position 330 at which an elastic wave can be propagated to a position such as the measurement point 301-1, a transmission focal point is tied to the position 330, and the transmission and reception control unit 20 is instructed to irradiate the position 330 with a radiation pressure ultrasonic wave 23 having a predetermined acoustic intensity (Step 805). In response to the instruction, the transmission and reception control unit 20 causes the transmission beam former 21 to generate a transmission signal for irradiating a predetermined position in the measurement range 300 with the radiation pressure ultrasonic wave 23 that generates acoustic radiation pressure, and outputs the generated transmission signal to the probe 10. The probe 10 transmits radiation pressure ultrasonic waves toward the transmission focal point 330 of the biological tissue 100. Accordingly, acoustic radiation pressure is generated in the biological tissue 100, the biological tissue 100 receives the pressure locally, and an elastic restoring force acts thereon. Therefore, an elastic wave is generated in the biological tissue 100. The elastic wave propagates radially from the transmission focal point 330 in the membranous biological tissue, and a surface wave among the elastic wave mainly propagates in the surface of the membranous biological tissue 100 and a shear wave mainly propagates in the central portion. FIGS. 9(a) and 9(b) illustrate a case in which a wavefront propagating rightward is measured.

The displacement measuring unit 32 transmits a measurement ultrasonic wave 24 to and receives the measurement ultrasonic wave 24 from the transmission and reception control unit 20, and measures a displacement of the tissue at positions such as the measurement points 301-1, 301-2, 311-1, and 311-2 disposed on both surfaces of the membranous biological tissue 100 (Steps 806 and 807). Accordingly, as shown in FIG. 3, the displacement of the measurement points 301-1, 301-2, 311-1, and 311-2 is measured at least at a certain time point. In FIG. 3, the displacement is measured in time series. Specifically, under the control of the transmission and reception control unit 20, the transmission beam former 21 generates a transmission signal and outputs the transmission signal to the probe 10. Accordingly, as shown in FIGS. 9(a) and 9(b), the probe 10 irradiates the plurality of measurement points 301 and the like with one or more measurement ultrasonic waves 24 at a predetermined timing, and receives echoes of the ultrasonic waves reflected from the measurement point 301 and the like by each transducer of the probe 10. The transmission and reception control unit 20 sets a plurality of reception scanning routes extending in a depth direction (z direction) through the plurality of measurement points 301 of the measurement ultrasonic wave 24, operates the reception beam former 22, and performs phasing addition of output signals of the transducers for a plurality of reception focal points on the reception scanning routes to generate reception focus data. The transmission and reception control unit 20 may repeat transmission of the measurement ultrasonic wave 24 and reception of the echo at predetermined time intervals to obtain a time change in the displacement of each measurement point 301-1 and the like as shown in FIG. 3.

In FIG. 9(a), the reception focus data is obtained by irradiating each of the plurality of measurement points 301 with the measurement ultrasonic wave 24 and setting a reception scanning route to the transmitted measurement point 301 each time. On the other hand, in FIG. 9(b), the reception focus data is obtained by irradiating a plurality of measurement points 301 with one measurement ultrasonic wave 24 and setting a reception scanning route to a plurality of measurement points 301 respectively. The transmission and reception pattern in FIG. 9(a) has excellent sensitivity and the transmission and reception pattern in FIG. 9(b) has a high temporal resolution. Any of the transmission and reception patterns shown in FIGS. 9(a) and 9(b) may be used depending on a position of the biological tissue 100 and a required temporal resolution.

The physical property evaluation unit 33 obtains velocities of elastic waves (mainly surface waves) $V_{z0}$, $V_{z1}$ propagating on a front surface side (depth $z=z_0$) and a back surface side ($z=z_1$) respectively, a ratio $V_{z0}/V_{z1}$, and a phase difference $\delta$ of elastic waves on the front surface side and the back surface side using the displacement of the measurement point 301 and the like on the front surface side and the back surface side obtained in Step 807. The measurement result of the displacement is three-dimensional information in a propagation direction x, a depth direction z, and a time direction t. The velocities can be calculated from a change in the propagation direction x and the time direction t, and the phase difference $\delta$ can be calculated by cross-correlation calculation between the depth direction z and the time direction t. The velocity V is an evaluation index indicating a difference in a viscoelastic modulus E, and the phase difference $\delta$ is an evaluation index indicating a difference in physical properties due to depth.

Specifically, when positions of the measurement points 301-1 and 301-2 on the front surface side (depth $z=z_0$) in an in-plane direction x of the biological tissue 100 are $x=x_0$ and $x=x_1$ respectively, the velocity $V_{z0}$ of the elastic wave propagating on the front surface side is expressed by Equation (1) if the displacement u at a time point t is expressed by u ($x_0$, $z_0$, t) and u ($x_1$, $z_0$, t) respectively. In Equation (1), $\Delta[a, b]$ indicates a difference between a and b, or a result of the cross-correlation calculation.

$$V_{z0} = \frac{\Delta[u(x_0, z_0, t), u(x_1, z_0, t)]}{x_0 - x_1} \tag{1}$$

Similarly, when positions of the measurement points 311-1 and 311-2 on the back surface side (depth $z=z_1$) of the biological tissue 100 in the direction x are $x=x_0$ and $x=x_1$ respectively, the displacement u of the measurement points 311-1 and 311-2 on the back surface side at the time point t is represented by u ($x_0$, $z_1$, t) and u ($x_1$, $z_1$, t) respectively, and the velocity $V_{z1}$ of the elastic wave propagating on the back surface side is expressed by Equation (2).

$$V_{z1} = \frac{\Delta[u(x_0, z_1, t), u(x_1, z_1, t)]}{x_0 - x_1} \tag{2}$$

The physical property evaluation unit 33 obtains the velocities $V_{z0}$ and $V_{z1}$ of elastic waves on the front surface side and the back surface side from the Equations (1) and (2), and further calculates the speed ratio $V_{z0}/V_{z1}$ (Steps 808 and 809). The physical property evaluation unit 33 may obtain the elastic modulus E by Equation (3).

$$E = 3\rho V^2 \tag{3}$$

In Equation (3), v is a velocity obtained by Equation (1) or Equation (2), and $\rho$ is a predetermined density.

As shown in FIG. 3, the physical property evaluation unit 33 obtains the phase difference $\delta$ between the displacement u of the measurement point 301 or the like on the front surface side and the displacement u of the measurement point 311 on the back surface side by the cross-correlation calculation (Steps 810 and 811) with Equation 4.

$$\delta = \Delta[u(x_0, z_0, t), u(x_0, z_1, t)] \tag{4}$$

The physical property evaluation unit 33 determines whether the organ constituted by the biological tissue 100 functions well using the calculated index value (speed V, speed ratio, phase difference $\delta$) indicating physical properties (Step 812). For example, whether the organ constituted by the biological tissue 100 functions well is determined by comparing a predetermined reference value for each organ with the calculated index value. For example, in an organ in which the tissue is preferably soft and likely to be deformed, when the viscoelastic modulus E obtained from the velocity V indicates that the tissue is softer than the reference value, it is determined that the organ functions well, and conversely, when the viscoelastic modulus E indicates that the tissue is harder than the reference value, it is determined that the organ does not function well. As shown in FIG. 10(a), the determination result can be superimposed on the image (B mode image) obtained in Step 802 and displayed on the display unit 15 by applying a color or pattern indicating whether the organ functions well to the membranous biological tissue 100 at the position of the measurement point (Step 813). As shown in FIG. 10(*b*), a color or a pattern indicating a magnitude of the index value and a comparison result (whether the organ functions well) between the index value and the reference value may be displayed for each of the measurement points 301 and 311 in the depth direction z and the propagation direction x of the biological tissue 100.

Further, when the biological tissue 100 is an organ having the space 100*a* therein, in Step 812, the physical property evaluation unit 33 may acquire the image generated in step 802 in time series, obtain the capacity by obtaining an area of the space 100*a*, and plot the index value (for example, speed V) at each time point and the capacity as shown in FIG. 7. By performing the plotting in each of contraction and expansion periods of the organ, it is possible to obtain the specific hysteresis of the organ, and to determine whether the organ functions well based on the shape and the area of the hysteresis, a contraction acceleration, and an expansion acceleration.

As described above, the ultrasonic diagnostic device according to the first embodiment can obtain and display an index value indicating physical properties of the membranous biological tissue 100. Furthermore, it is possible to determine and display whether the organ constituted by the biological tissue 100 functions well.

Second Embodiment

An operation example of each unit of an ultrasound diagnostic device according to the second embodiment will be described with reference to FIG. 11. The second embodiment describes an example in which an index value indicating physical properties of a surface of each of the adjacent biological tissues 100-1 and 100-2 is calculated to determine whether the biological tissue 100-1 and the biological tissue 100-2 are adhered. FIG. 11 is a flowchart showing an overall operation of the ultrasonic diagnostic device. Description of the same operations as those in the flow of FIG. 8 will be omitted in the flow of FIG. 11.

Similar to Steps 801 to 803 in the flow of FIG. 8, the control unit 30 generates images of the biological tissues 100-1 and 100-2 in the image acquisition range 400 and receives the measurement range 300 from the user. Then, the measurement point setting unit 31 extracts a boundary between the biological tissues 100-1 and 100-2 by processing the image of the measurement range 300, and sets the measurement points 301 and 302 on surfaces facing each other right across the boundary (Step 1104). Here, two or more measurement points 301 and 302 are set on the surfaces of the biological tissues 100-1 and 100-2 respectively. The measurement point 303 may be further set in the boundary layer 100-3 between the biological tissues 100-1 and 100-2.

Next, similarly to Steps 805 to 806 in FIG. 8, the displacement measuring unit 32 emits the radiation pressure ultrasound wave 23 from the probe 10 and propagates elastic waves to the biological tissues 100-1 and 100-2, and the measurement ultrasonic wave 24 is transmitted to and received by the biological tissues 100-1 and 100-2. Then, similarly to Step 807, tissue displacements of the plurality of measurement points 301 and 302 disposed on the boundary surface and the measurement point 303 disposed in the boundary layer 100-3 are measured in time series (Step 1107).

Similar to Steps 808 and 809 in FIG. 8, the physical property evaluation unit 33 obtains velocities $V_{z0}$, $V_{z1}$, and $V_{z2}$ of elastic waves (mainly surface waves) propagating through surfaces of the biological tissue 100-1, the boundary layer 100-3, and the surface of the biological tissue 100-2 with Equation (5) using displacement $u_0$ ($x_0$, $z_0$, t), $u_1$ ($x_0$, $z_1$, t), and $u_2$ ($x_0$, $z_2$, t) of the measurement points 301, 303, and 302 obtained in Step 807, and obtains corresponding ratios $V_{z0}/V_{z1}$, $V_{z0}/V_{z2}$, and $V_{z1}/V_{z2}$ (Steps 1108 and 1109).

$$V_{zi} = \frac{\Delta[u(x_0, z_i, t), u(x_1, z_i, t)]}{x_0 - x_1} \quad (5)$$

Further, by the same processing as in Steps 810 and 811 of FIG. 8, among the displacements $u_0$ ($x_0$, $z_0$, $u_1$ ($x_0$, $z_1$, t), and $u_2$ ($x_0$, $z_2$, t) due to elastic waves, a phase difference $\delta_{0-1}$ between $u_0$ ($x_0$, $z_0$, t) and $u_1$ ($x_0$, $z_1$, t), a phase difference $\delta_{1-2}$ between $u_1$ ($x_1$, $z_1$, t) and $u_2$ ($x_0$, $z_2$, t), and a phase difference $\delta_{0-2}$ between $u_0$ ($x_0$, $z_0$, t) and $u_2$ ($x_0$, $z_2$, t) are obtained by Equation (6) (Steps 1110, 1111).

$$\delta_{i\text{-}j} = \Delta[u(x_0, z_i, t), u(x_0, z_j, t)] \quad (6)$$

Further, the physical property evaluation unit 33 obtains amplitudes $A_{z0}$, $A_{z1}$, and $A_{z2}$ of the displacements $u_0$ ($x_0$, $z_0$, t), $u_1$ ($x_0$, $z_1$, t), and $u_2$ ($x_0$, $z_2$, t) of the measurement points 301, 303, and 302 and obtains corresponding ratios $A_{z0}/A_{z1}$, $A_{z0}/A_{z2}$, and $A_{z1}/A_{z2}$ (Steps 1112 and 1113).

The physical property evaluation unit 33 uses calculated index values (velocity V, velocity ratio, phase difference $\delta$, amplitude A, and amplitude ratio) representing physical properties to determine whether the boundaries of the biological tissues 100-1 and 100-2 are adhered (the boundary layer 100-3 is a viscoelastic membrane) or not (the boundary layer 100-3 is a liquid membrane) (Step 1114). In the case of adhesion, since the measurement points 301, 303 and 302 are integrated, displacements of the measurement points are highly correlated, as shown in FIGS. 5 (*a*) and 5 (*b*). Therefore, for example, the presence or absence of adhesion is determined by comparing the predetermined reference value with the calculated index value since adhesion can be determined when the velocity ratio and the amplitude ratio are close to 1 and the phase difference is small.

As shown in FIG. 12, the determination result can be superimposed on the image (B mode image) obtained in Step 802 and displayed on the display unit 15 by applying a color or pattern indicating whether the biological tissue 100-1 functions well at the position of the measurement point (Step 813).

Elastic waves (mainly surface waves here) generated in the biological tissue 100 includes a reflected wave that is reflected by a structure such as fibers or fat of the biological tissue 100 and propagates in a direction opposite to a direction of interest, and a refracted wave, a diffracted wave, or a scattered wave that is refracted, diffracted, or scattered by the structure, in addition to a main component (a transmitted wave) propagating in the direction of interest. Therefore, when the velocity of the entire elastic wave is measured at the measurement point 301 or the like set on the surface, the reflected wave, the refracted wave, the diffracted wave, or the scattered wave causes the velocity of the main component to be underestimated. Therefore, the displacement measuring unit 32 may extract the main component to reduce the influence of the reflected wave, the refracted wave, the diffracted wave, and the scattered wave and measure the velocity of the main component with high accuracy.

Specifically, the displacement measuring unit 32 obtains a frequency distribution of the displacement, and further selects a wave component having a predetermined intensity (amplitude) or more on a frequency basis. Therefore, the displacement measurement unit 32 can separate and extract the velocity component centering on the surface wave of the transmitted wave which is a main component from a reflected wave, a refracted wave, a diffracted wave, and a scattered wave.

The processing will be described in more detail with reference to FIG. 13. The displacement measuring unit 32 extracts spatio-temporal data (see FIG. 13(*b*)) with a specific depth $z=z_0$ from a time change of displacement (see FIG. 13(*a*)) of each point in a space (plane) having the propagation direction (x direction) of the elastic wave measured in steps 807 and 1107 in FIGS. 8 and 11 and the depth direction (z direction) as two axes. As shown in FIG. 13(*b*), the spatio-temporal data at the depth $z=z_0$ is expressed as a displacement (amplitude) of a plane having the time t and the propagation direction (x direction) as two axes. FIG. 13(*b*) shows an example in which there is no wave propagating in the direction opposite to the direction of interest, and only the main component (transmitted wave) 61 and the refracted wave, the diffracted wave, and the scattered wave 63 are propagated.

Next, the displacement measuring unit 32 performs a two-dimensional Fourier transform (2D-FFT) on the spatio-temporal data with the time t and the propagation direction (x direction) in FIG. 13(*b*) as two axes, and separates the spatio-temporal data into wave components represented by a time frequency f, a spatial frequency kx and intensity (amplitude) (FIG. 13(*c*)). As shown in FIG. 13(*c*), the data after 2D-FFT is an intensity (amplitude) distribution (hereinafter, also referred to as a frequency power distribution) of a wave component of a space (plane) having the time frequency f and the spatial frequency kx as two axes.

The displacement measuring unit 32 selects a wave component having a predetermined intensity or more from the frequency power distribution in FIG. 13(*c*) for each time frequency f or each spatial frequency kx by using a filter (FIGS. 13(*d*) and 13(*e*)). The filter of FIG. 13(*e*) sets a range 1301 including a point where the intensity (amplitude) of the wave component is largest for each time frequency f or spatial frequency kx, and only the wave component of the range 1301 is selected.

The wave component of the velocity centered on the transmitted wave which is the main component 61 of the frequency power distribution (FIG. 13(*e*)) of the range 1301 extracted by the filter is separated from the reflected wave 62, the refracted wave, the diffracted wave, and the scattered wave 63.

Next, the displacement measuring unit 32 performs two-dimensional inverse Fourier transform (2D-IFFT) on the frequency power distribution (FIG. 13(*e*)) extracted by the filter, and again returns to the displacement (amplitude) data of the plane having the time t and the propagation direction (x direction) as two axes (FIG. 13(*f*)).

The displacement measuring unit 32 repeats the processing of FIGS. 13(*a*) to 13(*e*) while gradually changing the depth z, and obtains displacement data for all depths (FIG. 13(*f*)). Accordingly, the velocity component centered on the surface wave of the transmitted wave can be separated and extracted from the reflected wave, the refracted wave, the diffracted wave, and the scattered wave. Therefore, the physical property evaluation unit 33 can calculate the velocity based on wavefront data (FIG. 13(*f*)) indicating the displacement (amplitude) the main component 61 in the depth direction (z direction), the propagation direction (x direction), and the time direction (t direction) generated by the displacement measurement unit 32.

According to the present embodiment described above, by measuring the surface wave, the membrane-like tissue in the biological body, properties of the surface of the tissue, and presence or absence of the function and bonding (for example, adhesion) of the organ constituted by the tissue can be evaluated with high accuracy by ultrasonic waves.

By using the ultrasonic diagnostic device according to the present embodiment, a doctor can detect an abnormality of a bladder or a heart early. In addition, since it is possible to determine the presence or absence of bonding (for example, adhesion) in the biological body, a device route can be confirmed before the laparoscopic surgery and the physical burden on the patient can be reduced.

REFERENCE SIGN LIST

1 ultrasonic diagnostic device
10 probe
13 input unit
15 display unit
16 memory
20 transmission and reception control unit
21 transmission beam former
22 reception beam former
30 control unit
31 measurement point setting unit
32 displacement measuring unit
33 physical property evaluation unit
34 image generation unit
100 inspection object (biological tissue)

The invention claimed is:

1. An ultrasonic diagnostic device comprising:
a probe;
a transmission beam former coupled to the probe;
a reception beam former coupled to the probe;
a display; and
a controller, the controller coupled to the probe, the transmission beam former, the reception beam former and the display, the controller configured to:
set four or more measurement points on a biological tissue to be inspected, the four or more measurement points include at least two first measurement points on a front surface of the biological tissue at a same first depth and at least two second measurement points on a back surface of the biological tissue at a same second depth,
measure a first displacement of the biological tissue from at least one of the at least two first measurement points by using a measurement ultrasonic wave received by the probe and measure a second displacement of the biological tissue from at least one of the at least two second measurement points by using the measurement ultrasonic wave,
calculate a first velocity of a first surface wave that propagates on the front surface of the biological tissue and a second velocity of a second surface wave that propagates on the back surface of the biological tissue, a ratio of the first velocity and the second velocity, and a phase difference of the first surface wave and the second surface wave based on the first displacement and the second displacement, wherein the first velocity and the second velocity are a first evaluation index and a second evaluation index, respectively, indicating a difference in a viscoelastic modulus, and the phase difference is a third evaluation index indicating a difference in physical properties of the biological tissue due to depth, wherein the controller is configured to:

compare the first evaluation index, the second evaluation index and the third evaluation index to respective predetermined references values to determine respective determination results indicating whether the biological tissue functions properly, and superimpose and display the determination results for each of the four or more measurement points in a depth direction and a propagation direction of the biological tissue and respective magnitudes of the first evaluation index, the second evaluation index and the third evaluation index on an image of the biological tissue on the display by applying respective colors or patterns.

2. The ultrasonic diagnostic device according to claim 1, wherein the controller unit sets the at least four measurement points based on the image of the biological tissue.

3. The ultrasonic diagnostic device according to claim 1, wherein the transmission beam former is configured to transmit an ultrasonic wave to the biological tissue, wherein the reception beam former is configured to receive an echo returning from the biological tissue, wherein the transmission beam former transmits a first ultrasonic wave that generates radiation pressure in the biological tissue and a second ultrasonic wave, as the measurement ultrasonic wave, that is used to measure respective displacements of the at least two first measurement points and the at least two second measurement points, and wherein the controller is configured to measure the first displacement and the second displacement by using a reception signal of the reception beam former that receives an echo of the second ultrasonic wave.

4. The ultrasound diagnostic device according to claim 3, wherein the transmission beam former transmits a third ultrasonic wave that is used to generate the image of the biological tissue, wherein the controller is configured to:

measure the first displacement and the second displacement by using a reception signal of the reception beam former, and generate the image of the biological tissue by using a reception signal output from the reception beam former unit that receives an echo of the third ultrasonic wave.

5. A method for evaluating physical properties of a biological tissue, the method comprising:

setting four or more measurement points on the biological tissue to be inspected, the four or more measurement points include at least two first measurement points on a front surface of the biological tissue at a same first depth and at least two second measurement points on a back surface of the biological tissue at a same second depth;

measuring, a first displacement of the biological tissue at the at least two first measurement points by using a measurement ultrasonic wave, and measuring a second displacement of the biological tissue at the at least two second measurement points by using the measurement ultrasonic wave; and calculating a first velocity of a first surface wave that propagates on the front surface of the biological tissue and a second velocity of a second surface wave that propagates on the back surface of the biological tissue, a ratio of the first velocity and the second velocity, and a phase difference of the first surface wave and the second surface wave based on the first displacement and the second displacement, wherein the first velocity and the second velocity are a first evaluation index and a second evaluation index, respectively, indicating a difference in a viscoelastic modulus, and the phase difference is a third evaluation index indicating a difference in physical properties of the biological tissue due to depth, wherein the method further comprises:

comparing the first evaluation index, the second evaluation index and the third evaluation index to respective predetermined references values to determine respective determination results indicating whether the biological tissue functions properly, and superimposing and displaying the determination results for each of the four or more measurement points in a depth direction and a propagation direction of the biological tissue and respective magnitudes of the first evaluation index, the second evaluation index and the third evaluation index on an image of the biological tissue on a display by applying respective colors or patterns.

* * * * *